United States Patent
Brendel

(10) Patent No.: US 7,035,077 B2
(45) Date of Patent: Apr. 25, 2006

(54) DEVICE TO PROTECT AN ACTIVE IMPLANTABLE MEDICAL DEVICE FEEDTHROUGH CAPACITOR FROM STRAY LASER WELD STRIKES, AND RELATED MANUFACTURING PROCESS

(75) Inventor: Richard L. Brendel, Carson City, NV (US)

(73) Assignee: Greatbatch-Sierra, Inc., Carson City, NV (US)

( * ) Notice: Subject to any disclaimer, the term of this patent is extended or adjusted under 35 U.S.C. 154(b) by 0 days.

(21) Appl. No.: 11/162,350

(22) Filed: Sep. 7, 2005

(65) Prior Publication Data

US 2006/0028784 A1    Feb. 9, 2006

Related U.S. Application Data

(63) Continuation-in-part of application No. 10/842,967, filed on May 10, 2004.

(60) Provisional application No. 60/607,841, filed on Sep. 7, 2004.

(51) Int. Cl.
*H01G 4/35* (2006.01)

(52) U.S. Cl. .......................... 361/302; 361/309; 607/5; 29/25.41

(58) Field of Classification Search ................. 361/302, 361/303, 304, 306.3, 307; 607/5, 3; 29/25.41, 29/25.42
See application file for complete search history.

(56) References Cited

U.S. PATENT DOCUMENTS

| | | |
|---|---|---|
| 2,756,375 A | 7/1956 | Peck |
| 3,235,939 A | 2/1966 | Rodriguez et al. |
| 3,538,464 A | 11/1970 | Walsh |
| 3,920,888 A | 11/1975 | Barr |
| 4,083,022 A | 4/1978 | Nijman |
| 4,144,509 A | 3/1979 | Boutros |
| 4,148,003 A | 4/1979 | Colburn et al. |
| 4,152,540 A | 5/1979 | Duncan et al. |
| 4,220,813 A | 9/1980 | Kyle |
| 4,247,881 A | 1/1981 | Coleman |
| 4,314,213 A | 2/1982 | Wakino |
| 4,352,951 A | 10/1982 | Kyle |
| 4,362,792 A | 12/1982 | Bowsky et al. |
| 4,421,947 A | 12/1983 | Kyle |
| 4,424,551 A * | 1/1984 | Stevenson et al. .......... 361/302 |
| 4,456,786 A | 6/1984 | Kyle |
| 4,737,601 A | 4/1988 | Gartzke |
| 4,741,710 A | 5/1988 | Hogan et al. |
| 5,032,692 A | 7/1991 | DeVolder |
| 5,070,605 A | 12/1991 | Daglow et al. |
| 5,142,430 A | 8/1992 | Anthony |
| 5,333,095 A | 7/1994 | Stevenson et al. |
| 5,440,447 A | 8/1995 | Shipman et al. |
| 5,539,611 A | 7/1996 | Hegner et al. |
| 5,670,063 A | 9/1997 | Hegner et al. |
| 5,751,539 A | 5/1998 | Stevenson et al. |

(Continued)

*Primary Examiner*—Anthony Dinkins
(74) *Attorney, Agent, or Firm*—Kelly Lowry & Kelley, LLP

(57) ABSTRACT

An insulative shield is co-bonded to the top of a ceramic capacitor in a feedthrough terminal assembly on an active implantable medical device. The insulative shield is a thin substrate that provides protection against damage and degradation of the feedthrough capacitor and/or its conformal coating from heat, splatter or debris resulting from the electromechanical connection of components during construction of the assembly. Laser welding, thermal or ultrasonic bonding, soldering, brazing or related lead attachment techniques can create such heat, splatter or debris. In a preferred embodiment, the insulative shield is co-bonded using the capacitor's own conformal coating.

44 Claims, 5 Drawing Sheets

U.S. PATENT DOCUMENTS

| | | |
|---|---|---|
| 5,825,608 A | 10/1998 | Duva et al. |
| 5,867,361 A | 2/1999 | Wolf et al. |
| 5,870,272 A | 2/1999 | Seifried et al. |
| 5,905,627 A | 5/1999 | Brendel et al. |
| 5,959,829 A | 9/1999 | Stevenson et al. |
| 5,973,906 A | 10/1999 | Stevenson et al. |
| 6,008,980 A | 12/1999 | Stevenson et al. |
| 6,031,710 A | 2/2000 | Wolf et al. |
| 6,275,369 B1 * | 8/2001 | Stevenson et al. .......... 361/302 |
| 6,349,025 B1 | 2/2002 | Fraley et al. |
| 6,414,835 B1 | 7/2002 | Wolf et al. |
| 6,424,234 B1 | 7/2002 | Stevenson |
| 6,529,103 B1 | 3/2003 | Brendel |
| 6,566,978 B1 | 5/2003 | Stevenson |
| 6,829,133 B1 * | 12/2004 | Wermer et al. .............. 361/302 |
| 6,963,482 B1 * | 11/2005 | Breyen et al. .............. 361/302 |
| 2002/0166618 A1 | 11/2002 | Wolf et al. |
| 2005/0201039 A1 * | 9/2005 | Stevenson et al. .......... 361/302 |

* cited by examiner

THERMOPLASTIC POLYMIDE SUPPORTED
TAPE ADHESIVE

| ABLELOC (R) 5500 MECHANICAL PROPERTIES | TEST METHODS |
|---|---|
| 90° Peel Strength - 250 mil (6.3 mm) width<br>Alloy 42 Substrate @ 25°C: 5.0 $lb_f$ (2.5 $kg_r$) peak<br>@ 230°C: 1.4 $lb_f$ (0.64 $kg_r$) peak<br><br>P I Coated Si Substrate @ 25°C: 5.5 $lb_f$ (2.5 $kg_r$) peak<br>@ 230°C: 1.2 $lb_f$ (0.55 $kg_r$) peak | MT-8 |
| Flatwise Tensile Strength - 250 $mil^2$ (6.3 $mm^2$)<br>Alloy 42 Substrate @ 25°C: 3300 psi (93 kg)<br>@ 230°C: 450 psi (13 kg)<br><br>(1) TH exposure - 16 hours, 85° C/85° RH | MT-1 |

FIG. 5

DEVICE TO PROTECT AN ACTIVE IMPLANTABLE MEDICAL DEVICE FEEDTHROUGH CAPACITOR FROM STRAY LASER WELD STRIKES, AND RELATED MANUFACTURING PROCESS

BACKGROUND OF THE INVENTION

This invention relates generally to electromagnetic interference (EMI) feedthrough terminal assemblies, and related methods of construction, designed to decouple and shield undesirable electromagnetic interference signals from associated active implantable medical devices (AIMDs), such as cardiac pacemakers, implantable defibrillators, cochlear implants, neurostimulators, active drug pumps, and the like. More particularly, the present invention relates to an improved EMI feedthrough terminal assembly that includes an insulating shield to prevent damage or degradation to a feedthrough capacitor or its adjunct conformal coating from lead assembly methods, including laser welding, thermal or ultrasonic bonding or the like.

Feedthrough terminal assemblies are generally well known in the art for conducting electrical signals through the housing or case of an electronic instrument. For example, in AIMDs, the feedthrough terminal assembly comprises one or more conductive terminal pins supported by an insulator structure for feedthrough passage from the exterior to the interior of the medical device. Many different insulator structures and related mounting methods are known for use in medical devices wherein the insulator structure provides a hermetic seal to prevent entry of body fluids into the housing of the medical device. In a cardiac pacemaker, for example, the feedthrough terminal pins are typically connected to one or more lead wires within the housing to conduct pacing pulses to cardiac tissue and/or detect or sense cardiac rhythms.

However, the lead wires can also undesirably act as an antenna and thus tend to collect stray EMI signals for transmission into the interior of the AIMD. It has been documented that pacemaker inhibition, asynchronous pacing and missed-beats can occur. All of these situations can be dangerous or even life threatening for a pacemaker dependent patient. In prior art devices, such as those shown in U.S. Pat. Nos. 5,333,095 and 4,424,551 (the contents of which are incorporated herein), the feedthrough terminal assembly has been combined in various ways with a ceramic feedthrough capacitor filter to decouple EMI signals to the grounded housing of the AIMD.

In general, the ceramic feedthrough capacitor has one or more passages or feedthrough holes and is connected to the hermetic terminal of the AIMD in a variety of ways. In order for the EMI filtered feedthrough capacitor to operate properly, a low-impedance, low-resistance electrical connection must be made between ground electrodes in the feedthrough capacitor and the ferrule of the feedthrough terminal assembly which in turn mechanically and electrically connects to the overall conductive housing of the AIMD.

For example, in a cardiac pacemaker, the feedthrough terminal assembly consists of a conductive ferrule generally made of titanium which is laser welded to the overall titanium housing of the AIMD. This not only provides a hermetic seal, but also makes the ferrule of the feedthrough terminal assembly a continuous part of the overall electromagnetic shield that protects the electronics of the AIMD from EMI. The ceramic feedthrough capacitor is, in turn, electrically and mechanically bonded to the ferrule of the hermetic terminal. In the past, and, in particular, as described in U.S. Pat. Nos. 5,333,095 and 4,424,551, the connection is typically performed using a thermal setting conductive adhesive. One such material is a silver flake loaded conductive polyimide.

The feedthrough terminal assembly consisting of the hermetic terminal with a mounted feedthrough capacitor contains one or more lead wires which must be connected to the internal circuitry of the AIMD. These circuit connections are typically done prior to the laser welding of the ferrule to the housing of the AIMD. Lead wire connections are performed in a number of ways, including flex cable connections, routing the lead wires to wire bond pads on a circuit board or substrate, or direct connection to hybrid chips of equivalent circuitry.

It is very important that surface insulation on the feedthrough capacitor and related terminal be in the hundreds or thousands of megaohms and be very reliable, rugged and stable. Degradation of insulation resistance or electrical failure of the feedthrough capacitor and/or the related feedthrough terminal assembly would lead to premature failure of the AIMD. For example, in the case of a cardiac pacemaker, the device could short out and cease its function in providing life saving pulses to the patient's heart.

In a higher voltage device, such as an implantable cardioverter defibrillator (ICD), it is extremely important that the surfaces of the feedthrough capacitor and related structures not be susceptive to high voltage electric arcing or flashover. When a ceramic feedthrough capacitor, which has a dielectric constant (K) of over 2000, operates at high voltage, there is a situation that is known as charge pooling which can occur on its surface. Where the high K ceramic dielectric material makes a transition to air, the dielectric constant changes suddenly from over 2000 to the permitivity of air which has a K of 1. This makes it very difficult for the electric fields to relax without creating microcolumb discharges, streamers or high voltage arcs. Accordingly, a common technique is to put a conformal coating over the top of the ceramic feedthrough capacitor. This can be in the form of a non-conductive polymer, such as a thermal setting epoxy or polyimide material. A convenient material for such purposes is a polyimide washer such as a thermal plastic polyimide supportive tape adhesive. One such material is manufactured by Ablestik (known as Ableloc® 5500). This material has a dielectric constant that is between 3 and 4 and serves to relax the high voltage fields.

However, it is very important that the conformal coating material not be damaged during installation of the feedthrough terminal assembly and its related components. Making lead attachments to circuits inside a pacemaker can cause heat, splatter or debris from the related coupling operations, i.e., welding, thermal or ultrasonic bonding, soldering, brazing, etc., to land on the capacitor's conformal coating. This heat, splatter or debris can cause localized melting or disruption of the conformal coating or embedding of metallic particles, all of which can lead to high voltage breakdown of the device. This can lead to immediate or delayed failure of the AIMD, which, as mentioned above, could be life threatening to a patient.

The conformal coatings that are used over feedthrough capacitors to prevent high voltage breakdown are typically quite thin. One reason for this is the need to keep AIMDs very small in size. Another reason is that these coatings do not have the same coefficient of thermal expansion as a barium titanate capacitor. Too thick of a conformal coating could lead to cracking of the dielectric in the feedthrough capacitor which can also cause reliability problems. Accordingly, there is a need for a design which will protect the surface of the feedthrough capacitor and/or its conformal coating from damage caused by lead attachment processes, including laser welding, thermal or ultrasonic bonding, soldering, brazing or the like.

SUMMARY OF THE INVENTION

The present invention is directed to a process for manufacturing a feedthrough terminal assembly for an active implantable medical device, comprising the steps of: associating a feedthrough capacitor with a conductive ferrule, the feedthrough capacitor having first and second sets of electrode plates, wherein the second set of electrode plates is conductively coupled to the ferrule; passing a terminal pin or leadwire through the ferrule in non-conductive relation, and through the feedthrough capacitor in conductive relation with the first set of electrode plates; placing an insulative shield over a surface of the feedthrough capacitor; and conductively coupling electronic circuitry for the active implantable medical device to the terminal pin or leadwire, wherein the insulative shield protects the surface of the feedthrough capacitor from heat, splatter or debris occasioned by said coupling of the electronic circuitry to the terminal pin or leadwire.

The insulative shield may comprise a circuit board, ceramic, alumina-oxide, Fosterite, alumina, BT epoxy, berrylia alumina oxide, polyimide, modified polyimide, cyanate ester, composite epoxy, multifunctional epoxy, tetra-functional epoxy, modified epoxy or standard epoxy. The circuit board may comprise a resin, i.e., epoxy, polyimide, or cyante ester, reinforced by fabric cloth, i.e., fiberglass.

The insulative shield may be co-bonded to a surface of the feedthrough capacitor by using a conformal coating on the feedthrough capacitor. The conformal coating may comprise a non-conductive polymer, a thermal setting epoxy, or a polyimide.

The feedthrough terminal assembly of the present invention may be used with an active implantable medical device such as a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

The conductive coupling of the electronic circuitry to the terminal pin or leadwire may comprise laser welding, thermal or ultrasonic bonding, soldering, or brazing, or the like. The process may further comprise the step of attaching a conductive pad, i.e. a wire bond pad, to the terminal pin or lead wire, wherein the electronic circuitry is conductively coupled to the conductive pad. The conductive pad may be supported in spaced relation above the feedthrough capacitor by means of an assembly housing over the feedthrough terminal assembly.

These and other aspects of the invention will be apparent to one skilled in the art in light of the following detailed description of the preferred embodiments.

BRIEF DESCRIPTION OF THE DRAWINGS

The accompanying drawings illustrate the invention. In such drawings:

FIG. 5 is a table of properties for the Ableloc® 5500 thermal plastic polyimide supported tape adhesive.

DETAILED DESCRIPTION OF THE PREFERRED EMBODIMENT

The present invention resides in a thin substrate or insulative shield co-bonded to the top surface of a feedthrough capacitor in a feedthrough filter assembly. The insulative shield provides protection from heat, splatter or debris from lead attachment techniques. The insulative shield is co-bonded using the capacitor's own conformal coating material. In this way, the high voltage electric fields contained within the feedthrough capacitor can still make a transition to a material having a low dielectric constant (K), before contacting air. In fact, the insulative shield has a much lower dielectric constant than the dielectric in the feedthrough capacitor, which also helps to relax the high voltage fields.

Figure 1:
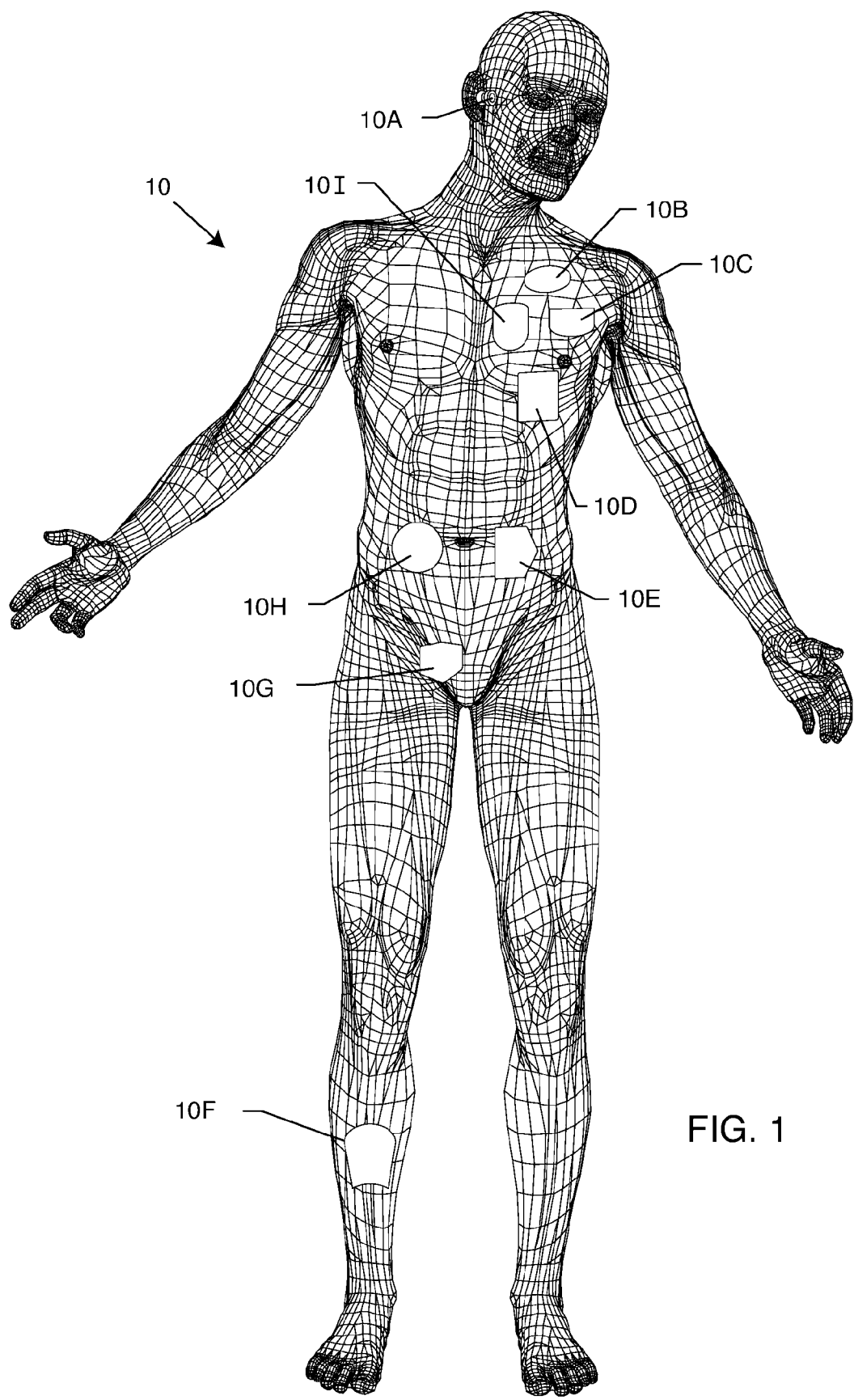
FIG. 1 is a schematic illustration of a human body illustrating various types and locations of active implantable medical devices currently in use.

FIG. 1 is a wire formed diagram of a generic human body showing a number of types and locations of active implantable medical devices 10. 10A is a family of hearing devices which can include the group of cochlear implants, piezeoelectric sound bridge transducers and the like. 10B includes an entire variety of neurostimulators and brain stimulators. Neurostimulators are used to stimulate the vagus nerve for example to treat epilepsy, obesity and depression. Brain stimulators are similar to a pacemaker but its electrodes are implanted deep into the brain for sensing the onset of the seizure and also providing electrical stimulation to brain tissue to prevent the seizure from actually happening. 10C shows a cardiac pacemaker which is well-known in the art. 10D includes the family of left ventricular assist devices (LVAD's), and artificial hearts. 10E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry. 10F includes a variety of bone growth stimulators for rapid healing of fractures. 10G includes urinary incontinence devices. 10H includes the family of pain relief spinal cord stimulators, anti-tremor stimulators and other types of neurostimulators used to block pain. 10I includes implantable cardioverter defibrillator (ICD) devices and also includes the family of congestive heart failure devices (CHF), otherwise known as cardio resynchronization therapy (CRT) devices.

Figure 2:
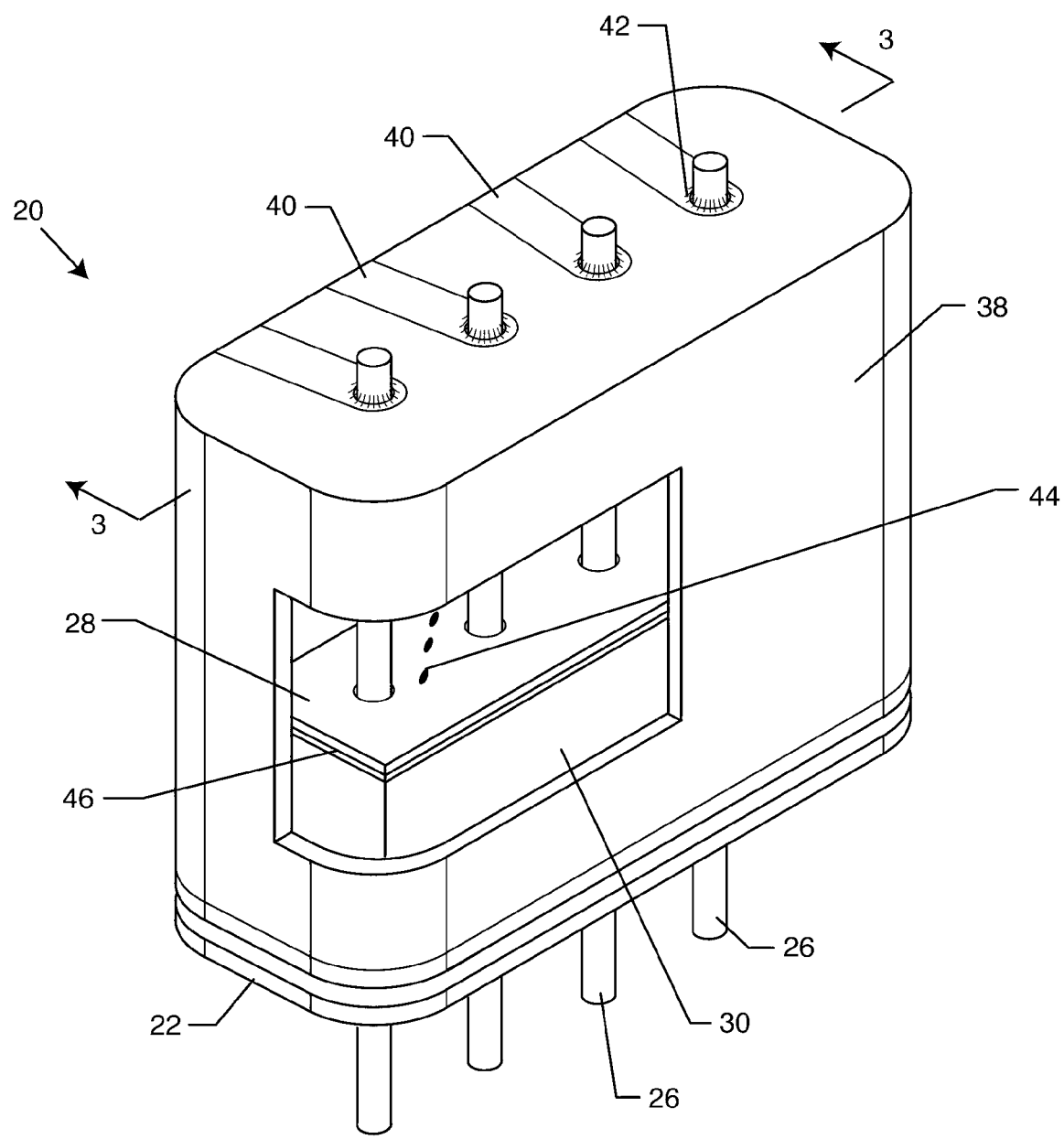
FIG. 2 is an elevated perspective view of a quad polar feedthrough terminal assembly of the present invention with a section of the housing cut-away.
Figure 3:
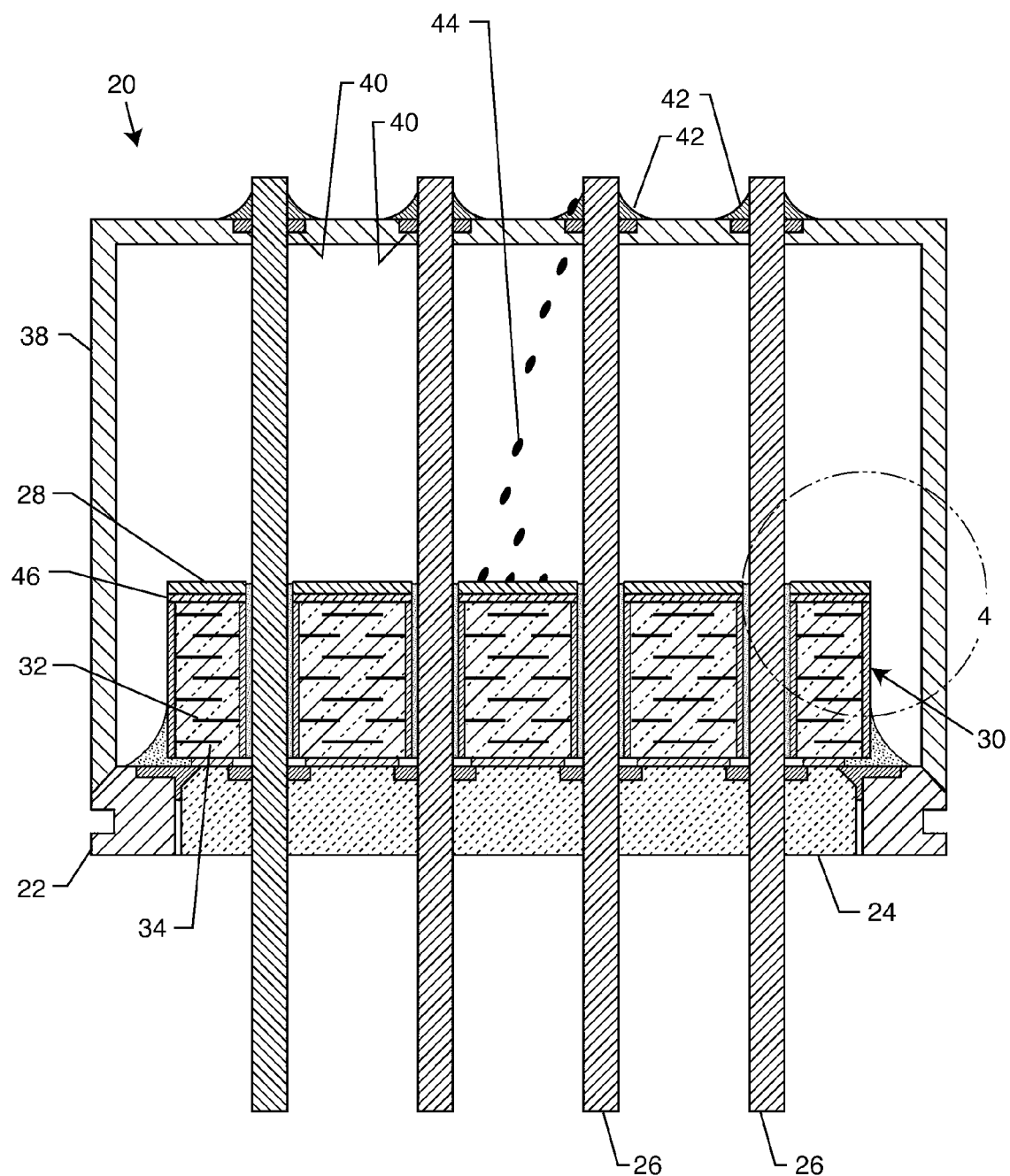
FIG. 3 is a cross-sectional view taken along line 3—3 of FIG. 2.
Figure 4:
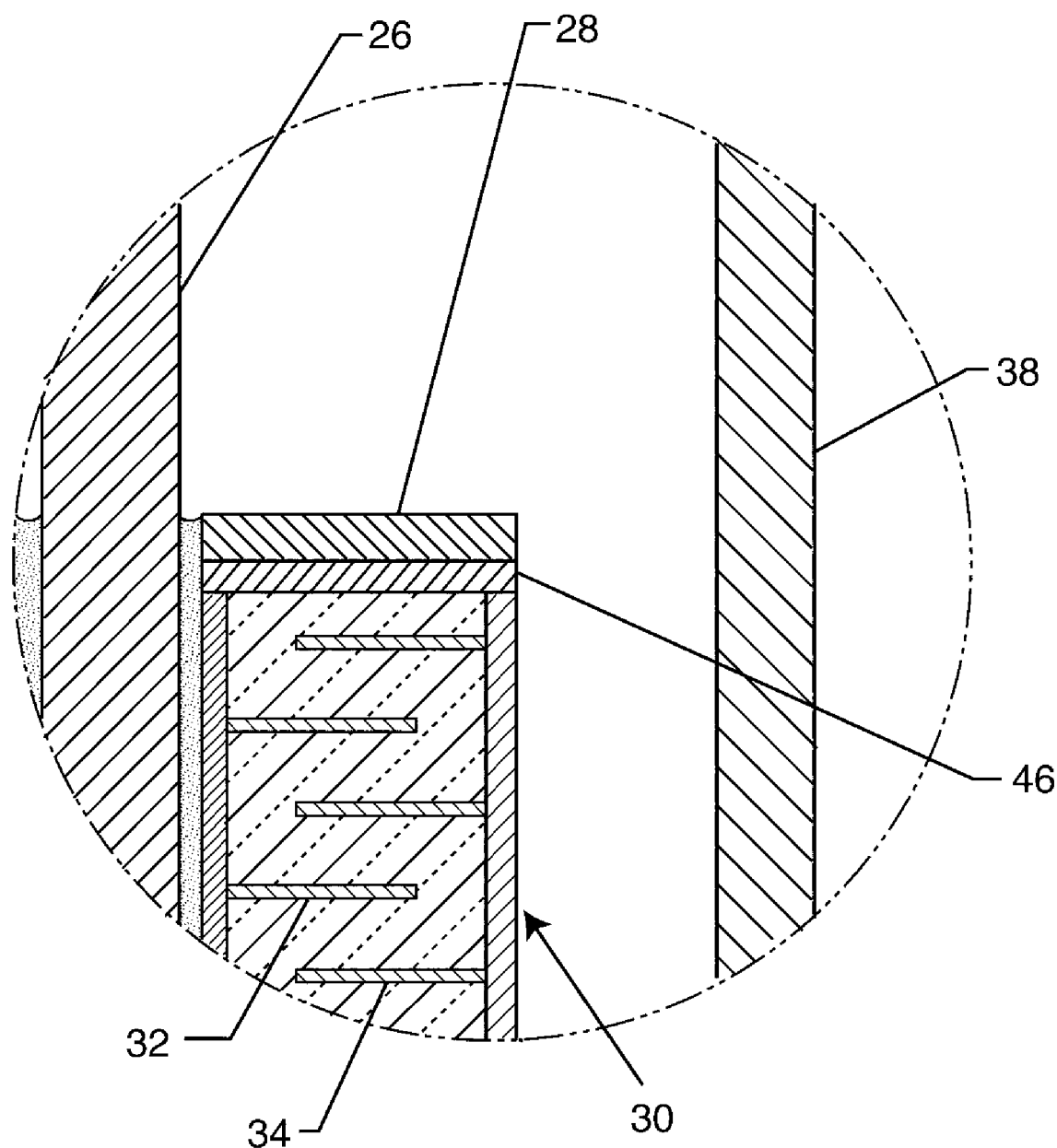
FIG. 4 is an enlarged sectional view of the area indicated by line 4 in FIG. 3.

FIG. 2 is an isometric view of a feedthrough terminal assembly 20 of the present invention. FIGS. 3 and 4 show cross-sectional views of the feedthrough terminal assembly 20 shown in FIG. 2. In the preferred embodiment, the feedthrough terminal assembly 20 comprises a conductive ferrule 22, an insulator 24, terminal pins or leadwires 26, a feedthrough capacitor 30, an insulative shield 28, and conductive pads 40. The feed through capacitor 30 includes a first set of electrode plates 32 interleaved with a second set of electrode plates 34. The first set of electrode plates 32 are conductively coupled to the terminal pin or leadwires 26. The second set of electrode plates 34 are conductively coupled to a ground plane, i.e., the ferrule 22. The insulator 24 is connected to the terminal pins or leadwires 26 by means of a gold braze 36. The conductive pads 40 are conductively coupled to the terminal pins or leadwires 26 and to electronic circuitry (not shown) for the active implantable medical device 10. The insulative shield 28 is co-bonded to the feedthrough capacitor 30 by a conformal coating 46 on the surface of the feedthrough capacitor 30. This is best seen in the exploded view shown in FIG. 4.

FIG. 2, illustrates an assembly housing 38 surrounding the entire feedthrough terminal assembly 20 and four conductive pads 40 on top of the housing 38. For purposes of illustration only, a portion of the housing 38 is cutaway to expose the top surface of the feedthrough capacitor 30 having the insulative shield 28. The housing 38 can typically be of ceramic, plastic or other insulative materials. Housing 38 forms a rigid structure for supporting the conductive pads 40, i.e., wire bond pads in spaced relation above the capacitor 30, as shown. These wire bond pads 40 are typically molded into or adhesively bonded to the housing 38. As previously described in U.S. Ser. No. 10/842,967, filed May 10, 2004, the wire bond pads 40 are typically made of Kovar which are then overplated with nickel and then ultra pure soft gold. The housing 38, which is used to support the wire bond pads 40 as shown, is not necessary to practice the present invention.

As seen in FIG. 2, the conductive pad 40 is electrically and mechanically coupled to the terminal pin or leadwires 26 by laser welding, thermal or ultrasonic bonding, soldering, brazing, or the like, which makes a solid mechanical and electrical connection 42. This connection 42 also serves to hold the housing 38 firmly in place on the feedthrough terminal assembly 20. The creation of this connection 42 can result in heat, splatter or debris 44 that can impact upon the top surface of the feedthrough capacitor 30. This heat, splatter or debris 44 can have a damaging or degrading effect on the feedthrough capacitor 30, as described below. In accordance with the present invention, the insulative shield 28 protects the top surface of the feedthrough capacitor 30. Specifically, the insulative shield 28 protects the conformal coating 46 on the top surface of the feedthrough capacitor 30. As will be discussed below, since alumina is a very high temperature material, the heat, splatter or debris 44 is prevented from reaching the feedthrough capacitor 30 or conformal coating 46 by the insulative shield 28.

In FIG. 4, one can see the feedthrough capacitor 30, conformal coating 46 and insulative shield 28. Conformal coating 46 is best formed from a thermal plastic polyimide supported tape adhesive. Such a material is manufactured by Ablestik and is known as Ableloc® 5500. The properties of this material are described in co-pending U.S. Ser. No. 10/842,967, filed May 10, 2004 and herein in FIG. 5.

Referring now back to FIG. 2, the insulative shield 28 protects the conformal coating 46 and capacitor 30 so that they will not be damaged or degraded by heat, splatter or debris 44 from the formation of connections 42. As mentioned above, connections 42 are not limited only to laser welding but also include thermal or ultrasonic bonding, brazing, soldering, conductive thermal setting polymers, or the like.

The insulative shield 28 of the present invention may be comprised of ceramics, polyimides, cyanate esters and BT epoxies. As described herein, the insulative shield 28 can include any of the ceramic or non-ceramic materials discussed below, in addition to many others that have been and will be described. The insulative shield 28 should be relatively thin and must have a high structural integrity. In the preferred embodiment, the insulative shield 28 is a thin sheet of alumina ceramic. Alumina ceramic can be made quite thin, has very high mechanical strength and is very inexpensive to manufacture. Typically, alumina is a common circuit board material. The use of an alumina wire bond pad has been thoroughly described in co-pending application U.S. Ser. No. 10/842,967, filed May 10, 2004.

Ideal ceramic materials for the insulative shield 28 include, but are not limited to the group of: alumina-oxide, Fosterite, alumina in various purities, berrylia and aluminum nitride. These ceramic substrates are well known in the art, have good mechanical and laser scribe characteristics and do not greatly mismatch the thermal coefficient of expansion of the feedthrough capacitor 30 and therefore will prevent the formation of excessive mechanical stresses that could fracture the feedthrough capacitor 30. For ceramic substrates, the scribe characteristics of the ceramic materials is important so that the individual substrates of the present invention can be cut or snapped out of a larger production array of said substrates.

Non-ceramic printed circuit board materials can also be used as a circuit board substitute for the insulative shield 28. Such materials are mostly constructed from a resin reinforced by a fabric cloth. Epoxy (FR-4), polyimide and cyanate ester are the more common resin systems available today. Fiberglass is the most popular fabric. It is important that the insulative shield 28 be able to withstand high temperatures caused by laser welding of the terminal pins or leadwires 26 of the feedthrough terminal assembly 20.

Non-ceramic circuit board temperature ranges are most often expressed as the glass transition temperature (Tg) of the material. The material's Tg is the point above which the mechanical and electrical properties of the material begin to rapidly deteriorate. Printed circuit board materials change from hard, brittle substances to soft, rubber like substances after they reach their glass transition temperature. Tg ratings can vary anywhere from around 115° C. all the way up to 270° C. for these systems (ref. the Tg table in U.S. Ser. No. 10/842,967, filed May 10, 2004). These include polyimides, modified polyimides, cyanate esters, BT epoxies, composite epoxies, multifunctional epoxies, tetra-functional epoxies, modified FR-4s and standard FR-4s.

The conformal coating 46 that bonds the insulative shield 28 to the feedthrough capacitor 30 should be somewhat flexible and stress absorbing. The flexibility of the conformal coating 46 will help prevent cracking of the feedthrough capacitor 30 due to any mismatches in the thermal coefficients of expansion. Accordingly, in the preferred embodiment, the conformal coating 46 is a polyimide in that it forms a ring type molecule after it goes through its glass transition temperature of approximately 260° C. Compared to an epoxy, polyimide can absorb stresses and is quite resilient.

A process for manufacturing a feedthrough terminal assembly 20 for an active implantable medical device 10, comprises the steps of:

associating the feedthrough capacitor 30 with the conductive ferrule 22, the feedthrough capacitor 30 having first and second sets of electrode plates 32, 34, wherein the second set of electrode plates 34 is conductively coupled to the ferrule 22;

passing the terminal pin or leadwire 26 through the ferrule 22 in non-conductive relation, and through the feedthrough capacitor 30 in conductive relation with the first set of electrode plates 32;

placing the insulative shield 28 over the top surface of the feedthrough capacitor 30;

co-bonding the insulative shield 28 to the feedthrough capacitor 30 using the conformal coating 46 on the feedthrough capacitor 30;

laser welding, thermal or ultrasonic bonding, soldering, or brazing the conductive pad 40 to the terminal pin or lead wire 26, wherein electronic circuitry (not shown) for the active implantable medical device 1 0 is conductively coupled to the conductive pad 40 and the conductive pad 40 is conductively coupled to the terminal pin or leadwire 26 and wherein the insulative shield 28 protects the surface of the feedthrough capacitor 30 or conformal coating 46 from heat, splatter or debris 44 occasioned by said coupling of the electronic circuitry (not shown) to the terminal pin or leadwire 26; and supporting the conductive pad 40 in spaced relation above the feedthrough capacitor 30 by the assembly housing 38 over the feedthrough terminal assembly 20.

The present invention may be practiced in combination with an active implantable medical device 10 such as a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

Although various embodiments have been described in detail for purposes of illustration, various modifications may be made without departing from the scope and spirit of the invention.

What is claimed is:

1. A process for manufacturing a feedthrough terminal assembly for an active implantable medical device, comprising the steps of:
    associating a feedthrough capacitor with a conductive ferrule, the feedthrough capacitor having first and second sets of electrode plates, wherein the second set of electrode plates is conductively coupled to the ferrule;
    passing a terminal pin or leadwire through the ferrule in non-conductive relation and through the feedthrough capacitor in conductive relation with the first set of electrode plates;
    placing an insulative shield over a surface of the feedthrough capacitor; and
    conductively coupling electronic circuitry for the active implantable medical device to the terminal pin or leadwire, wherein the insulative shield protects the surface of the feedthrough capacitor from heat, splatter or debris occasioned by said coupling of the electronic circuitry to the terminal pin or leadwire.

2. The process of claim 1, wherein the insulative shield comprises a circuit board, ceramic, alumina-oxide, Fosterite, alumina, BT epoxy, berrylia alumina oxide, polyimide, modified polyimide, cyanate ester, composite epoxy, multifunctional epoxy, tetra-functional epoxy, modified epoxy or standard epoxy.

3. The process of claim 2, wherein the circuit board comprises resin reinforced by fabric cloth.

4. The process of claim 3, wherein the resin comprises epoxy, polyimide, or cyanate ester.

5. The process of claim 3, wherein the fabric cloth comprises fiberglass.

6. The process of claim 1, including the step of co-bonding the insulative shield to the feedthrough capacitor using a conformal coating on the feedthrough capacitor.

7. The process of claim 6, wherein the conformal coating comprises a non-conductive polymer, a thermal setting epoxy, or a polyimide.

8. The process of claim 1, wherein the active implantable medical device comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

9. The process of claim 1, wherein the conductive coupling comprises laser welding, thermal or ultrasonic bonding, soldering, or brazing.

10. The process of claim 1, including the step of attaching a conductive pad to the terminal pin or lead wire, wherein the electronic circuitry is conductively coupled to the conductive pad.

11. The process of claim 10, including the step of supporting the conductive pad in spaced relation above the feedthrough capacitor by an assembly housing over the feedthrough terminal assembly.

12. The process of claim 10, wherein the conductive pad comprises a wire bond pad.

13. A process for manufacturing a feedthrough terminal assembly for an active implantable medical device, comprising the steps of:
    associating a feedthrough capacitor with a conductive ferrule, the feedthrough capacitor having first and second sets of electrode plates, wherein the second set of electrode plates is conductively coupled to the ferrule;
    passing a terminal pin or leadwire through the ferrule in non-conductive relation and through the feedthrough capacitor in conductive relation with the first set of electrode plates;
    placing an insulative shield over a surface of the feedthrough capacitor;
    co-bonding the insulative shield to the feedthrough capacitor using a conformal coating on the feedthrough capacitor; and
    laser welding, thermal or ultrasonic bonding, soldering, or brazing electronic circuitry for the active implantable medical device to the terminal pin or leadwire, wherein the insulative shield protects the surface of the feedthrough capacitor from heat, splatter or debris occasioned by said coupling of the electronic circuitry to the terminal pin or leadwire.

14. The process of claim 13, wherein the insulative shield comprises a circuit board, ceramic, alumina-oxide, Fosterite, alumina, BT epoxy, berrylia alumina oxide, polyimide, modified polyimide, cyanate ester, composite epoxy, multifunctional epoxy, tetra-functional epoxy, modified epoxy or standard epoxy.

15. The process of claim 14, wherein the circuit board comprises resin reinforced by fabric cloth.

16. The process of claim 15, wherein the resin comprises epoxy, polyimide, or cyanate ester.

17. The process of claim 15, wherein the fabric cloth comprises fiberglass.

18. The process of claim 13, wherein the conformal coating comprises a non-conductive polymer, a thermal setting epoxy, or a polyimide.

19. The process of claim 13, wherein the active implantable medical device comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

20. The process of claim 13, including the step of attaching a conductive pad to the terminal pin or lead wire, wherein the electronic circuitry is conductively coupled to the conductive pad.

21. The process of claim 20, including the step of supporting the conductive pad in spaced relation above the feedthrough capacitor by an assembly housing over the feedthrough terminal assembly.

22. The process of claim 20, wherein the conductive pad comprises a wire bond pad.

23. A feedthrough terminal assembly for an active implantable medical device, comprising:
   a feedthrough capacitor having first and second sets of electrode plates, wherein the second set of electrode plates is conductively coupled to a conductive ferrule;
   a terminal pin or leadwire passing through the conductive ferrule in non-conductive relation and through the feedthrough capacitor in conductive relation with the first set of electrode plates;
   an insulative shield on a surface of the feedthrough capacitor; and
   electronic circuitry for the active implantable medical device conductively coupled to the terminal pin or leadwire, wherein the insulative shield protects the surface of the feedthrough capacitor from heat, splatter or debris occasioned by said coupling of the electronic circuitry to the terminal pin or leadwire.

24. The feedthrough terminal assembly of claim 23, wherein the insulative shield comprises a circuit board, ceramic, alumina-oxide, Fosterite, alumina, BT epoxy, berrylia alumina oxide, polyimide, modified polyimide, cyanate ester, composite epoxy, multifunctional epoxy, tetra-functional epoxy, modified epoxy or standard epoxy.

25. The feedthrough terminal assembly of claim 24, wherein the circuit board comprises resin reinforced by fabric cloth.

26. The feedthrough terminal assembly of claim 25, wherein the resin comprises epoxy, polyimide, or cyanate ester.

27. The feedthrough terminal assembly of claim 25, wherein the fabric cloth comprises fiberglass.

28. The feedthrough terminal assembly of claim 23, including a conformal coating on the feedthrough capacitor, wherein the conformal coating co-bonds the insulative shield to the feedthrough capacitor.

29. The feedthrough terminal assembly of claim 28, wherein the conformal coating comprises a non-conductive polymer, a thermal setting epoxy, or a polyimide.

30. The feedthrough terminal assembly of claim 23, wherein the active implantable medical device comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

31. The feedthrough terminal assembly of claim 23, wherein the electronic circuitry is conductively coupled to the terminal pin or leadwire by laser welding, thermal or ultrasonic bonding, soldering, or brazing.

32. The process of claim 23, including a conductive pad conductively coupled to the terminal pin or lead wire and conductively coupled to the electronic circuitry.

33. The process of claim 32, including an assembly housing over the feedthrough terminal assembly, wherein the assembly housing supports the conductive pad in spaced relation above the feedthrough capacitor.

34. The process of claim 32, wherein the conductive pad comprises a wire bond pad.

35. A feedthrough terminal assembly for an active implantable medical device, comprising:
   a feedthrough capacitor having first and second sets of electrode plates, wherein the second set of electrode plates is conductively coupled to a conductive ferrule;
   a terminal pin or leadwire passing through the conductive ferrule in non-conductive relation and through the feedthrough capacitor in conductive relation with the first set of electrode plates;
   an insulative shield on a surface of the feedthrough capacitor;
   a conformal coating on the feedthrough capacitor, wherein the conformal coating co-bonds the insulative shield to the feedthrough capacitor; and
   electronic circuitry for the active implantable medical device conductively coupled to the terminal pin or leadwire by laser welding, thermal or ultrasonic bonding, soldering, or brazing, wherein the insulative shield protects the surface of the feedthrough capacitor from heat, splatter or debris occasioned by said coupling of the electronic circuitry to the terminal pin or leadwire.

36. The feedthrough terminal assembly of claim 35, wherein the insulative shield comprises a circuit board, ceramic, alumina-oxide, Fosterite, alumina, BT epoxy, berrylia alumina oxide, polyimide, modified polyimide, cyanate ester, composite epoxy, multifunctional epoxy, tetra-functional epoxy, modified epoxy or standard epoxy.

37. The feedthrough terminal assembly of claim 36, wherein the circuit board comprises resin reinforced by fabric cloth.

38. The feedthrough terminal assembly of claim 36, wherein the resin comprises epoxy, polyimide, or cyanate ester.

39. The feedthrough terminal assembly of claim 36, wherein the fabric cloth comprises fiberglass.

40. The feedthrough terminal assembly of claim 35, wherein the conformal coating comprises a non-conductive polymer, a thermal setting epoxy, or a polyimide.

41. The feedthrough terminal assembly of claim 35, wherein the active implantable medical device comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

42. The process of claim 35, including a conductive pad conductively coupled to the terminal pin or lead wire and conductively coupled to the electronic circuitry.

43. The process of claim 42, including an assembly housing over the feedthrough terminal assembly, wherein the assembly housing supports the conductive pad in spaced relation above the feedthrough capacitor.

44. The process of claim 42, wherein the conductive pad comprises a wire bond pad.

* * * * *